(12) United States Patent
Nagai et al.

(10) Patent No.: US 8,137,938 B2
(45) Date of Patent: Mar. 20, 2012

(54) METHOD FOR PRODUCING AN L-AMINO ACID

(75) Inventors: Yuri Nagai, Kawasaki (JP); Yoshihiro Usuda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/749,932

(22) Filed: Mar. 30, 2010

(65) Prior Publication Data

US 2010/0221792 A1    Sep. 2, 2010

Related U.S. Application Data

(63) Continuation of application No. PCT/JP2008/069070, filed on Oct. 14, 2008.

(60) Provisional application No. 60/980,744, filed on Oct. 17, 2007.

(30) Foreign Application Priority Data

Oct. 17, 2007  (JP) .................................. 2007-270272

(51) Int. Cl.
  *C12P 13/04*  (2006.01)
  *C12P 13/24*  (2006.01)
  *C12P 13/22*  (2006.01)

(52) U.S. Cl. .......... 435/106; 435/107; 435/115; 435/18; 435/199

(58) Field of Classification Search .................. 435/106, 435/107, 115, 18, 199
See application file for complete search history.

(56) References Cited

U.S. PATENT DOCUMENTS

| | | | |
|---|---|---|---|
| 6,911,332 B2 | 6/2005 | Usuda et al. | |
| 7,026,149 B2 | 4/2006 | Usuda et al. | |
| 7,029,893 B2 | 4/2006 | Usuda et al. | |
| 7,060,475 B2 | 6/2006 | Usuda et al. | |
| 7,192,748 B2 | 3/2007 | Usuda et al. | |
| 7,220,570 B2 | 5/2007 | Usuda et al. | |
| 7,306,933 B2 | 12/2007 | Van Dien et al. | |
| 7,468,262 B2 | 12/2008 | Usuda et al. | |
| 2005/0233308 A1 | 10/2005 | Nishio et al. | |
| 2006/0234356 A1 | 10/2006 | Usuda et al. | |
| 2006/0234357 A1 | 10/2006 | Usuda et al. | |
| 2007/0249017 A1 | 10/2007 | Usuda et al. | |
| 2009/0068712 A1 | 3/2009 | Terashita et al. | |
| 2009/0093029 A1 | 4/2009 | Usuda et al. | |
| 2009/0104667 A1 | 4/2009 | Asakura et al. | |
| 2009/0148915 A1 | 6/2009 | Van Dien et al. | |
| 2009/0203090 A1 | 8/2009 | Ptitsyn et al. | |
| 2009/0239269 A1 | 9/2009 | Tajima et al. | |
| 2009/0246835 A1 | 10/2009 | Iwatani et al. | |
| 2009/0291478 A1 | 11/2009 | Usuda et al. | |
| 2010/0047878 A1 | 2/2010 | Nagai et al. | |
| 2010/0062497 A1 | 3/2010 | Shiraga et al. | |

FOREIGN PATENT DOCUMENTS

| | | | |
|---|---|---|---|
| EP | 1715055 | | 10/2006 |
| EP | 1715056 | | 10/2006 |
| JP | 2005-333855 | | 12/2005 |
| JP | 2005333855 | A * | 12/2005 |
| WO | WO2007/100009 | | 9/2007 |

OTHER PUBLICATIONS

Sakai, T., et al., "Increased production of pyruvic acid by *Escherichia coli* RNase G mutants in combination with *cra* mutations," Appl. Microbiol. Biotechnol. 2007;76:183-192.
International Search Report and Written Opinion for PCT Patent App. No. PCT/JP2008/069070 (Feb. 17, 2009).

* cited by examiner

*Primary Examiner* — Tekchand Saidha
(74) *Attorney, Agent, or Firm* — Shelly Guest Cermak; Cermak Nakajima LLP

(57) ABSTRACT

An L-amino acid is produced by culturing a bacterium belonging to the family Enterobacteriaceae, which is able to produce the L-amino acid, and is modified so that the activity of ribonuclease G is decreased in a medium containing glycerol as the carbon source, and collecting the L-amino acid from the culture.

7 Claims, No Drawings

SEQUENCE LISTING

```
<160> NUMBER OF SEQ ID NOS: 4

<210> SEQ ID NO 1
<211> LENGTH: 1470
<212> TYPE: DNA
<213> ORGANISM: Escherichia coli
<220> FEATURE:
<221> NAME/KEY: CDS
<222> LOCATION: (1)..(1470)

<400> SEQUENCE: 1 atg acg gct gaa ttg tta gta aac gta acg cct tcg gaa acg cga gtg      48
Met Thr Ala Glu Leu Leu Val Asn Val Thr Pro Ser Glu Thr Arg Val
1               5                  10                  15 gcg tat att gat ggc ggt att ctg cag gaa att cat att gaa cgt gag      96
Ala Tyr Ile Asp Gly Gly Ile Leu Gln Glu Ile His Ile Glu Arg Glu
            20                  25                  30 gcg cga cgc gga ata gta ggc aat atc tac aag ggt cgt gta agt cgt     144
Ala Arg Arg Gly Ile Val Gly Asn Ile Tyr Lys Gly Arg Val Ser Arg
        35                  40                  45 gta ctt ccg ggt atg cag gcg gct ttt gta gat att ggg ctg gat aaa     192
Val Leu Pro Gly Met Gln Ala Ala Phe Val Asp Ile Gly Leu Asp Lys
    50                  55                  60 gcc gcg ttt ctt cat gca tcc gac atc atg ccg cac acc gaa tgt gtg     240
Ala Ala Phe Leu His Ala Ser Asp Ile Met Pro His Thr Glu Cys Val
65                  70                  75                  80 gcg ggt gaa gaa caa aag caa ttc acg gtg cgc gac atc tcg gaa ctg     288
Ala Gly Glu Glu Gln Lys Gln Phe Thr Val Arg Asp Ile Ser Glu Leu
                85                  90                  95 gtt cgt cag ggg caa gat ctg atg gtg cag gtg gtg aaa gat ccg ctt     336
Val Arg Gln Gly Gln Asp Leu Met Val Gln Val Val Lys Asp Pro Leu
            100                 105                 110 ggc act aaa ggt gcg cgc ctg acc acc gat atc acg ctc cct tct cgc     384
Gly Thr Lys Gly Ala Arg Leu Thr Thr Asp Ile Thr Leu Pro Ser Arg
        115                 120                 125
```

```
tat ctg gtg ttt atg cca ggg gct tct cac gtt ggg gtt tcc caa cgt        432
Tyr Leu Val Phe Met Pro Gly Ala Ser His Val Gly Val Ser Gln Arg
    130                 135                 140 att gaa agc gaa tca gaa cgt gaa cgc ctg aaa aaa gtg gtc gca gag        480
Ile Glu Ser Glu Ser Glu Arg Glu Arg Leu Lys Lys Val Val Ala Glu
145                 150                 155                 160 tat tgc gac gag cag ggc ggg ttt atc atc cgt acc gca gcg gaa ggg        528
Tyr Cys Asp Glu Gln Gly Gly Phe Ile Ile Arg Thr Ala Ala Glu Gly
                165                 170                 175 gtt ggc gag gct gaa ctg gcc tcc gat gcc gct tat ctg aaa cgc gtc        576
Val Gly Glu Ala Glu Leu Ala Ser Asp Ala Ala Tyr Leu Lys Arg Val
            180                 185                 190 tgg acc aaa gtt atg gag cgt aaa aaa cgc ccg cag acc cgt tat cag        624
Trp Thr Lys Val Met Glu Arg Lys Lys Arg Pro Gln Thr Arg Tyr Gln
        195                 200                 205 ctg tac ggc gaa ctg gcg ctg gcg cag cgt gtt ctg cgt gat ttc gcc        672
Leu Tyr Gly Glu Leu Ala Leu Ala Gln Arg Val Leu Arg Asp Phe Ala
    210                 215                 220 gat gcc gaa ctg gac cgc att cgc gtt gac tca cgc ctg act tac gaa        720
Asp Ala Glu Leu Asp Arg Ile Arg Val Asp Ser Arg Leu Thr Tyr Glu
225                 230                 235                 240 gcg tta ctt gag ttc acc tcg gag tac att ccc gag atg aca agc aag        768
Ala Leu Leu Glu Phe Thr Ser Glu Tyr Ile Pro Glu Met Thr Ser Lys
                245                 250                 255 ctg gag cat tac aca gga cgc cag ccg att ttc gat ctc ttt gat gtc        816
Leu Glu His Tyr Thr Gly Arg Gln Pro Ile Phe Asp Leu Phe Asp Val
            260                 265                 270 gaa aac gaa atc cag cga gcg ctg gaa cgc aaa gta gaa ctg aaa tcc        864
Glu Asn Glu Ile Gln Arg Ala Leu Glu Arg Lys Val Glu Leu Lys Ser
        275                 280                 285 ggt ggt tat ctc att atc gac cag acc gaa gcg atg acc acc gtg gac        912
Gly Gly Tyr Leu Ile Ile Asp Gln Thr Glu Ala Met Thr Thr Val Asp
    290                 295                 300 atc aat acc gga gcg ttt gtc ggt cat cgc aat ctg gac gac acc att        960
Ile Asn Thr Gly Ala Phe Val Gly His Arg Asn Leu Asp Asp Thr Ile
305                 310                 315                 320 ttc aat acc aat att gaa gcg acg cag gct atc gct cgc cag tta cgg       1008
Phe Asn Thr Asn Ile Glu Ala Thr Gln Ala Ile Ala Arg Gln Leu Arg
                325                 330                 335 ttg cgt aat ctg ggc ggg att atc att att gat ttc atc gat atg aat       1056
Leu Arg Asn Leu Gly Gly Ile Ile Ile Ile Asp Phe Ile Asp Met Asn
            340                 345                 350 aat gaa gat cac cgc cgc cga gtg ctg cac tcg ctg gag cag gcg ttg       1104
Asn Glu Asp His Arg Arg Arg Val Leu His Ser Leu Glu Gln Ala Leu
        355                 360                 365 agc aaa gac cgg gtg aaa acc agc gtt aat ggt ttt tcg gcg ctg ggg       1152
Ser Lys Asp Arg Val Lys Thr Ser Val Asn Gly Phe Ser Ala Leu Gly
    370                 375                 380 ctg gtg gag atg acg cgt aaa cgc acc cgc gaa agc att gag cac gta       1200
Leu Val Glu Met Thr Arg Lys Arg Thr Arg Glu Ser Ile Glu His Val
385                 390                 395                 400 ctg tgt aac gaa tgc cca acc tgc cac ggt cgc gga acg gtg aaa acc       1248
Leu Cys Asn Glu Cys Pro Thr Cys His Gly Arg Gly Thr Val Lys Thr
                405                 410                 415
```

-continued

| | | | | | | | | | | | | | |
|---|---|---|---|---|---|---|---|---|---|---|---|---|---|
| gtg | gaa | acg | gta | tgc | tat | gaa | atc | atg | cgc | gag | att | gtt | cgt gtc cac | 1296 |
| Val | Glu | Thr | Val | Cys | Tyr | Glu | Ile | Met | Arg | Glu | Ile | Val | Arg Val His | |
| | | | 420 | | | | 425 | | | | | 430 | | |

| cat | gct | tac | gac | tcc | gac | cgt | ttc | ctg | gtc | tat | gct | tct | ccg gca gta | 1344 |
| His | Ala | Tyr | Asp | Ser | Asp | Arg | Phe | Leu | Val | Tyr | Ala | Ser | Pro Ala Val | |
| | | | 435 | | | | 440 | | | | | 445 | | |

| gct | gaa | gcc | ttg | aaa | ggc | gaa | gag | tca | cac | tcg | ctg | gcg | gaa gtg gaa | 1392 |
| Ala | Glu | Ala | Leu | Lys | Gly | Glu | Glu | Ser | His | Ser | Leu | Ala | Glu Val Glu | |
| | | 450 | | | | | 455 | | | | | 460 | | |

| att | ttc | gtt | ggc | aaa | cag | gtt | aaa | gta | caa | att | gaa | ccg | ctc tat aac | 1440 |
| Ile | Phe | Val | Gly | Lys | Gln | Val | Lys | Val | Gln | Ile | Glu | Pro | Leu Tyr Asn | |
| 465 | | | | | 470 | | | | | 475 | | | 480 | |

| cag | gag | cag | ttt | gac | gtc | gta | atg | atg | taa | | | | | 1470 |
| Gln | Glu | Gln | Phe | Asp | Val | Val | Met | Met | | | | | | |
| | | | | 485 | | | | | | | | | | |

<210> SEQ ID NO 2
<211> LENGTH: 489
<212> TYPE: PRT
<213> ORGANISM: Escherichia coli

<400> SEQUENCE: 2

Met Thr Ala Glu Leu Leu Val Asn Val Thr Pro Ser Glu Thr Arg Val
1               5                   10                  15

Ala Tyr Ile Asp Gly Gly Ile Leu Gln Glu Ile His Ile Glu Arg Glu
            20                  25                  30

Ala Arg Arg Gly Ile Val Gly Asn Ile Tyr Lys Gly Arg Val Ser Arg
        35                  40                  45

Val Leu Pro Gly Met Gln Ala Ala Phe Val Asp Ile Gly Leu Asp Lys
    50                  55                  60

Ala Ala Phe Leu His Ala Ser Asp Ile Met Pro His Thr Glu Cys Val
65                  70                  75                  80

Ala Gly Glu Glu Gln Lys Gln Phe Thr Val Arg Asp Ile Ser Glu Leu
                85                  90                  95

Val Arg Gln Gly Gln Asp Leu Met Val Gln Val Val Lys Asp Pro Leu
            100                 105                 110

Gly Thr Lys Gly Ala Arg Leu Thr Thr Asp Ile Thr Leu Pro Ser Arg
        115                 120                 125

Tyr Leu Val Phe Met Pro Gly Ala Ser His Val Gly Val Ser Gln Arg
    130                 135                 140

Ile Glu Ser Glu Ser Glu Arg Glu Arg Leu Lys Lys Val Val Ala Glu
145                 150                 155                 160

Tyr Cys Asp Glu Gln Gly Gly Phe Ile Ile Arg Thr Ala Ala Glu Gly
                165                 170                 175

Val Gly Glu Ala Glu Leu Ala Ser Asp Ala Ala Tyr Leu Lys Arg Val
            180                 185                 190

Trp Thr Lys Val Met Glu Arg Lys Lys Arg Pro Gln Thr Arg Tyr Gln
        195                 200                 205

Leu Tyr Gly Glu Leu Ala Leu Ala Gln Arg Val Leu Arg Asp Phe Ala
    210                 215                 220

Asp Ala Glu Leu Asp Arg Ile Arg Val Asp Ser Arg Leu Thr Tyr Glu
225                 230                 235                 240

Ala Leu Leu Glu Phe Thr Ser Glu Tyr Ile Pro Glu Met Thr Ser Lys
                245                 250                 255

```
Leu Glu His Tyr Thr Gly Arg Gln Pro Ile Phe Asp Leu Phe Asp Val
            260                 265                 270

Glu Asn Glu Ile Gln Arg Ala Leu Glu Arg Lys Val Glu Leu Lys Ser
        275                 280                 285

Gly Gly Tyr Leu Ile Ile Asp Gln Thr Glu Ala Met Thr Thr Val Asp
        290                 295                 300

Ile Asn Thr Gly Ala Phe Val Gly His Arg Asn Leu Asp Asp Thr Ile
305                 310                 315                 320

Phe Asn Thr Asn Ile Glu Ala Thr Gln Ala Ile Ala Arg Gln Leu Arg
                325                 330                 335

Leu Arg Asn Leu Gly Gly Ile Ile Ile Asp Phe Ile Asp Met Asn
            340                 345                 350

Asn Glu Asp His Arg Arg Val Leu His Ser Leu Glu Gln Ala Leu
            355                 360                 365

Ser Lys Asp Arg Val Lys Thr Ser Val Asn Gly Phe Ser Ala Leu Gly
        370                 375                 380

Leu Val Glu Met Thr Arg Lys Arg Thr Arg Glu Ser Ile Glu His Val
385                 390                 395                 400

Leu Cys Asn Glu Cys Pro Thr Cys His Gly Arg Gly Thr Val Lys Thr
                405                 410                 415

Val Glu Thr Val Cys Tyr Glu Ile Met Arg Glu Ile Val Arg Val His
                420                 425                 430

His Ala Tyr Asp Ser Asp Arg Phe Leu Val Tyr Ala Ser Pro Ala Val
            435                 440                 445

Ala Glu Ala Leu Lys Gly Glu Glu Ser His Ser Leu Ala Glu Val Glu
        450                 455                 460

Ile Phe Val Gly Lys Gln Val Lys Val Gln Ile Glu Pro Leu Tyr Asn
465                 470                 475                 480

Gln Glu Gln Phe Asp Val Val Met Met
                485

<210> SEQ ID NO 3
<211> LENGTH: 59
<212> TYPE: DNA
<213> ORGANISM: Artificial sequence
<220> FEATURE:
<223> OTHER INFORMATION: primer

<400> SEQUENCE: 3
cattacgacg tcaaactgct cctggttata gagcggttca atgaagcctg ctttttat      59

<210> SEQ ID NO 4
<211> LENGTH: 58
<212> TYPE: DNA
<213> ORGANISM: Artificial sequence
<220> FEATURE:
<223> OTHER INFORMATION: primer

<400> SEQUENCE: 4
agggataaac atgacggctg aattgttagt aaacgtaacg cgctcaagtt agtataaa      58
```

METHOD FOR PRODUCING AN L-AMINO ACID

This application is a continuation under 35 U.S.C. §120 to PCT Patent Application No. PCT/JP2008/069070, filed on Oct. 14, 2008, which claims priority under 35 U.S.C. §119 to Japanese Patent Application No. 2007-270272, filed Oct. 17, 2007, and U.S. Provisional Patent Application No. 60/980,744, filed on Oct. 17, 2007, all of which are incorporated by reference. The Sequence Listing filed electronically herewith is also hereby incorporated by reference in its entirety (File Name: 20100330T_US-373_Seq_List; File Size: 12 KB; Date Created: Mar. 30, 2010).

BACKGROUND OF THE INVENTION

1. Field of the Invention

The present invention relates to a method for producing an L-amino acid using a microorganism. L-amino acids are useful in various applications, such as for ingredients in seasonings, food additives, feed additives, chemicals, and drugs.

2. Brief Description of the Related Art

L-amino acids are industrially produced by fermentation using microorganisms, such as those belonging to the genus Brevibacterium, Corynebacterium, Escherichia, or the like. In such production methods, bacterial strains isolated from nature, artificial mutants of such strains, and microorganisms modified by recombinant DNA techniques so that the activity of a basic L-amino acid biosynthesis enzyme is increased, and so forth have been used (EP0643135B, EP0733712B, EP1477565A, EP0796912A, EP0837134A, WO01/53459, EP1170376A, WO2005/010175, and WO96/17930).

When amino acids are produced using a microorganism, sugars are generally used in the medium as a carbon source, but glycerol has also been used as the carbon source (EP1715055A, EP1715056A).

Ribonuclease G was found to be involved in the maturation of the 5' end of 16S rRNA (EMBO J., 18 (1999) 2878-2885, Biochem. Biophys. Res. Commun., 259 (1999) 483-488). Furthermore, it is known that ribonuclease G digests an AU-rich region of a single stranded RNA, but the digestion sequence or other details have not yet been elucidated (J. Biol. Chem., 269 (1994) 10797-10803, J. Biol. Chem., 269 (1994) 10790-10796, J. Biol. Chem., 275 (2000) 8726-8732).

Ribonuclease G is highly homologous to the catalytic domain of ribonuclease E. This catalytic domain is located at the N-terminus of ribonuclease E, and this enzyme has been shown to be a major ribonuclease of *E. coli*. Ribonuclease E is involved in the decomposition of most of mRNAs, as well as the maturation of tRNAs and rRNAs (Genetics, 90 (1978) 659-671, J. Mol. Biol., 129 (1979) 343-357, Cell, 15 (1978) 1055-1066, RNA, 8 (2002) 97-109, Genes Dev., 16 (2002) 1102-1115, J. Mol. Biol., 352 (2005) 22-27). However, it has been found that ribonuclease G does not participate in the maturation of tRNAs and can only partially complement the lethality of *E. coli* in the absence of the ribonuclease E (EMBO J., 18 (1999) 2878-2885, Biochem. Biophys. Res. Commun., 259 (1999) 483-488).

Since a deficiency of the rng gene coding for ribonuclease G does not affect growth at all under typical laboratory conditions, the ribonuclease E can complement the function of ribonuclease G (EMBO J., 18 (1999) 2878-2885, Biochem. Biophys. Res. Commun., 259 (1999) 483-488, Mol. Gen. Genet., 253 (1997) 515-519).

Although there are a few reports about the physiological role of ribonuclease G, this enzyme has been reported to participate in the decomposition of eno mRNA or adhE mRNA, and to participate in the specific decomposition of mRNAs of multiple genes, including the genes coding for several glycolytic enzymes, on the basis of results of microarray analysis (Mol. Microbiol., 43 (2002) 1445-1456, Genes Cell., 6 (2001) 403-410, Biosci. Biotechnol. Biochem., 66 (2002) 2216-2220).

Moreover, when a strain deficient in both the rng and cra genes is cultured using glucose as the carbon source, pyruvic acid is produced (Appl. Microbiol. Biotechnol., 76 (2007) 183-192).

Furthermore, if the rng gene is deleted in an *Escherichia* bacterium, pyruvic acid and L-valine are produced (Japanese Patent Application Laid-open (Kokai, JP-A) No. 2005-333855).

SUMMARY OF THE INVENTION

An aspect of the present invention is an improved method for producing an L-amino acid by fermentation using a medium containing glycerol as the carbon source.

It has been found that by reducing the activity of ribonuclease G, the ability to produce an L-amino acid from glycerol in enterobacteria could be markedly improved.

It is an aspect of the present invention to provide a method for producing an L-amino acid comprising culturing a bacterium in a medium containing glycerol, wherein said bacterium belongs to the family Enterobacteriaceae and is able to produce the L-amino acid, and collecting the L-amino acid from the culture, wherein the bacterium has been modified so that the activity of ribonuclease G is decreased.

It is a further aspect of the present invention to provide the method as described above, wherein the rng gene coding for the ribonuclease G is inactivated.

It is a further aspect of the present invention to provide the method as described above, wherein the rng gene comprises a DNA coding for the amino acid sequence of SEQ ID NO: 2 or a variant thereof.

It is a further aspect of the present invention to provide the method as described above, wherein the L-amino acid is selected from the group consisting of L-lysine, L-glutamic acid, L-threonine, L-arginine, L-histidine, L-isoleucine, L-valine, L-leucine, L-phenylalanine, L-tyrosine, L-tryptophan, L-proline, L-cysteine, and combinations thereof.

It is a further aspect of the present invention to provide the method as described above, wherein the L-amino acid is L-lysine, and in the bacterium the activity of an enzyme is increased and/or the activity of lysine decarboxylase is decreased; wherein the enzyme is selected from the group consisting of dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, succinyl diaminopimelate deacylase, and combinations thereof.

It is a further aspect of the present invention to provide the method as described above, wherein the L-amino acid is L-threonine and in the bacterium the activity of an enzyme is increased; wherein the enzyme is selected from the group consisting of aspartate semialdehyde dehydrogenase, aspartokinase I, homoserine kinase, aspartate aminotransferase, threonine synthase, and combinations thereof.

It is a further aspect of the present invention to provide the method as described above, wherein the bacterium belongs to a genus selected from the group consisting of *Escherichia*, *Enterobacter*, and *Pantoea*.

It is a further aspect of the present invention to provide the method as described above, wherein glycerol is crude glycerol produced in biodiesel fuel production.

Still other objects, features, and attendant advantages of the present invention will become apparent to those skilled in the art from a reading of the following detailed description of embodiments constructed in accordance therewith, taken in conjunction with the accompanying drawings.

DETAILED DESCRIPTION OF EXEMPLARY EMBODIMENTS

<1> Glycerol

"Glycerol" refers to a substance of the nomenclatural name of propane-1,2,3-triol. Crude glycerol refers to industrially produced glycerol, which can also contain impurities. Crude glycerol is industrially produced by hydrolyzing fats and oils with water at a high temperature and under high pressure, or by the esterification reaction for biodiesel fuel production. Biodiesel fuel includes aliphatic acid methyl esters produced from fats and oils and methanol produced by a transesterification. Crude glycerol is a by-product of this reaction (refer to Fukuda, H., Kondo, A., and Noda, H., 2001, J. Biosci. Bioeng., 92, 405-416). In the biodiesel fuel production process, the alkaline catalyst method is used for the transesterification in many cases, and acids are added for neutralization. Therefore, crude glycerol of a purity of about 70 to 95% by weight, and also containing water and impurities, can be produced. Crude glycerol produced in the biodiesel fuel production process contains, in addition to water, residual methanol, alkali salts such as NaOH which act as a catalyst, and impurities including acids such as $K_2SO_4$, which is used for neutralizing the alkali. Although it depends on manufacturers and production methods, the amounts of these salts and methanol can reach several percent. The crude glycerol can contain ions from the alkali and the neutralization acid, such as sodium ions, potassium ions, chloride ions, and sulfate ions, in an amount of 2 to 7%, 3 to 6% in another example, 4 to 5.8% in another example, based on the weight of the crude glycerol. Although methanol can be absent, it can be present in an amount of 0.01% or less.

The crude glycerol may further contain trace amounts of metals, organic acids, phosphorus, aliphatic acids, and so forth. Examples of the organic acids include formic acid, acetic acid, and so forth, and although they can be absent, they can be present in an amount of 0.01% or less. Examples of trace metals required for growth of the microorganism include magnesium, iron, calcium, manganese, copper, zinc, and so forth. Magnesium, iron, and calcium can be present in an amount of 0.00001 to 0.1%, 0.0005 to 0.1% in another example, 0.004 to 0.05% in another example, and 0.007 to 0.01% in another example, in terms of the total amount based on the weight of the crude glycerol. Manganese, copper, and zinc can be present in the amount of 0.000005 to 0.01%, 0.000007 to 0.005% in another example, 0.00001 to 0.001% in yet another example, in terms of the total amount.

The purity of the crude glycerol can be 10% or higher in one example, 50% or higher in another example, 70% or higher in another example, or even 80% or higher in another example. As long as the impurities are within the aforementioned range, the purity of the glycerol can also be 90% or higher.

Crude glycerol produced in the production of biodiesel fuel is can be used. Particularly, crude glycerol which enables production of more L-amino acid can be used, compared with when using an equal weight of reagent glycerol. To produce more L-amino acid as compared with reagent glycerol can mean to increase the amino acid production amount by 5% or more in one example, 10% or more in another example, 20% or more in yet another example, compared with when reagent glycerol is used as the carbon source. "Reagent glycerol" means glycerol marketed as regent grade, or which has a purity equivalent to the purity of glycerol marketed as regent grade. The glycerol can have a purity of 99% by weight or higher, and pure glycerol can also be used. The expression "reagent glycerol in the same amount as crude glycerol" means that the reagent glycerol is the same weight as crude glycerol except for water, when the crude glycerol contains water.

Crude glycerol may be diluted with a solvent such as water. In such a case, the aforementioned descriptions concerning the amount of glycerol and impurities can be applied to the crude glycerol before dilution. That is, when a solution of crude glycerol in a solvent is used and the solvent is reduced so that it is 30% by weight or less, 20% by weight or less in another example, 10% by weight or less in another example, if the content of glycerol and any impurities are within the aforementioned ranges, this crude glycerol corresponds to the "crude glycerol" as described herein.

<2> Bacterium Belonging to the Family Enterobacteriaceae

The bacterium in accordance with the presently described subject matter belongs to the family Enterobacteriaceae, which has an ability to produce an L-amino acid, and has been modified so that activity of the ribonuclease G is decreased. The bacterium can be obtained by modifying a bacterium belonging to the family Enterobacteriaceae so that the activity of the ribonuclease G is decreased. Bacteria which can be modified so that the activity of the ribonuclease G is decreased and methods for imparting or enhancing L-amino acid-producing ability will be exemplified below. The bacterium can also be obtained by imparting an L-amino acid-producing ability to a bacterium which belongs to the family Enterobacteriaceae and has been modified so that the activity of the ribonuclease G is decreased, or by enhancing an L-amino acid-producing ability of a bacterium which belongs to the family Enterobacteriaceae and has been modified so that the activity of the ribonuclease G is decreased.

<2-1> Bacteria Used as the Parent Strain

A bacterium belonging to the family Enterobacteriaceae and having an L-amino acid-producing ability can be used.

The family Enterobacteriaceae includes bacteria belonging to the genera *Escherichia, Enterobacter, Erwinia, Klebsiella, Pantoea, Photorhabdus, Providencia, Salmonella, Serratia, Shigella, Morganella, Yersinia*, and so forth. In particular, bacteria classified into the family Enterobacteriaceae according to the taxonomy used by the NCBI (National Center for Biotechnology Information) database (http://www.ncbi.nlm.nih.gov/Taxonomy/Browser/wwwtax.cgi?id=91347) can be used.

A "bacterium belonging to the genus *Escherichia*" means that the bacterium is classified into the genus *Escherichia* according to the classification known to a person skilled in the art of microbiology, although the bacterium is not particularly limited. Examples of the bacterium belonging to the genus *Escherichia* include, but are not limited to, *Escherichia coli* (*E. coli*).

The bacterium belonging to the genus *Escherichia* is not particularly limited. However, examples include bacteria of the phyletic groups described in the work of Neidhardt et al. (Neidhardt F. C. Ed., 1996, *Escherichia coli* and *Salmonella*: Cellular and Molecular Biology/Second Edition, pp. 2477-2483, Table 1, American Society for Microbiology Press, Washington, D.C.). Specific examples include *Escherichia* coli W3110 (ATCC 27325), *Escherichia coli* MG1655 (ATCC 47076), and so forth, all of which can be derived from the prototype wild-type strain, K12.

These strains are available from, for example, the American Type Culture Collection (Address: P.O. Box 1549, Manassas, Va. 20108, United States of America). That is, an accession number is given to each strain, and these numbers can be used to order the desired strain. The accession numbers of the strains are listed in the catalogue of the American Type Culture Collection.

A bacterium belonging to the genus *Pantoea* means that the bacterium is classified into the genus *Pantoea* according to the classification known to a person skilled in the art of microbiology. Some species of *Enterobacter agglomerans* have been recently re-classified into *Pantoea agglomerans*, *Pantoea ananatis*, *Pantoea stewartii* or the like, based on nucleotide sequence analysis of 16S rRNA etc. (Int. J. Syst. Bacteriol., 43, 162-173 (1993)). Bacteria belonging to the genus *Pantoea* include such bacteria re-classified into the genus *Pantoea* as described above.

In the bacterium, in order to enhance glycerol assimilability, expression of the glpR gene (EP 1715056) can be attenuated, or expression of the glycerol metabolism genes (EP 1715055 A), such as glpA, glpB, glpC, glpD, glpE, glpF, glpG, glpK, glpQ, glpT, glpX, tpiA, gldA, dhaK, dhaL, dhaM, dhaR, fsa, and talC can be enhanced. A gene which encodes a mutant glycerol kinase resistant to inhibition by fructose-1, 6-bisphosphate can be enhanced (Pettigrew, D. W., Liu, W. Z., Holmes, C., Meadow, N. D., and Roseman, S., J. Bacteriol. 178, 10, 2846-52 (1996), Honisch, C. et. al., Genome Reseasch, 14: 2495-2502 (2004), WO2008/081959 and WO2008/107277). Furthermore, the activities of glycerol dehydrogenase and dihydroxyacetone kinase can be enhanced (WO2008/102861).

The expression "bacterium having an L-amino acid-producing ability (is able to produce an L-amino acid)" means a bacterium which can produce and secrete an L-amino acid in a medium when it is cultured in the medium. It can also mean a bacterium which can produce the objective L-amino acid in the medium in an amount not less than 0.5 g/L, or not less than 1.0 g/L in another example. The "L-amino acid" can include L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine.

Hereinafter, methods for imparting an L-amino acid-producing ability to such bacteria as mentioned above, or methods for enhancing an L-amino acid-producing ability of such bacteria as mentioned above are described.

To impart the ability to produce an L-amino acid, methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can be applied. Such methods include by acquiring an auxotrophic mutant, an L-amino acid analogue-resistant strain, or a metabolic regulation mutant, or by constructing a recombinant strain which overexpresses an L-amino acid biosynthetic enzyme. When breeding L-amino acid-producing bacteria, one or more of these properties may be imparted. The expression of L-amino acid biosynthetic enzyme(s) can be increased singly or in combinations of two or more. Furthermore, the impartation of these properties may be combined with the enhancement of the biosynthetic enzymes.

An auxotrophic mutant strain, L-amino acid analogue-resistant strain, or metabolic regulation mutant strain with the ability to produce an L-amino acid can be obtained by subjecting a parent strain or wild-type strain to a conventional mutatagenesis treatment, such as by exposure to X-rays or UV irradiation, or by treating the bacteria with a mutagen such as N-methyl-N'-nitro-N-nitrosoguanidine, etc., and then selecting those strains which exhibit the desired characteristics and also have the ability to produce an L-amino acid.

Moreover, the L-amino acid-producing ability can also be imparted or enhanced by increasing the enzymatic activity by gene recombination. An example of the method for increasing enzymatic activity includes modifying the bacterium so that the expression of a gene coding for an enzyme involved in the biosynthesis of an L-amino acid is enhanced. Gene expression can also be increased by 1) introducing an amplification plasmid prepared by introducing a DNA fragment containing the gene into a plasmid which contains, for example, at least a gene responsible for replication and proliferation of the plasmid in the microorganism, 2) increasing the copy number of the gene on the chromosome by conjugation, transfer, or the like, or 3) introducing a mutation into the promoter region of the gene (refer to International Patent Publication WO95/34672).

When the objective gene is introduced into the aforementioned amplification plasmid or chromosome, any promoter can be used to increase expression of the gene so long as the chosen promoter functions in the coryneform bacteria. The promoter can be the native promoter for the gene, or a modified promoter. The expression of a gene can also be controlled by suitably choosing a promoter that is strong and potent in coryneform bacteria, or by making the −35 and −10 regions of the promoter closer to the consensus sequence. These methods are fully described in International Patent Publication WO00/18935, European Patent Publication No. 1010755, and so forth.

Specific methods for imparting an L-amino acid-producing ability to bacteria and bacteria imparted with L-amino acid-producing ability are exemplified below.

L-Threonine-Producing Bacteria

Examples of microorganisms which are able to produce L-threonine include bacteria in which one or more activities of L-threonine biosynthesis system enzymes are enhanced. Examples of L-threonine biosynthetic enzymes include aspartokinase III (lysC), aspartate semialdehyde dehydrogenase (asd), aspartokinase I (thrA), homoserine kinase (thrB), threonine synthase (thrC), and aspartate aminotransferase (aspartate transaminase) (aspC). The parentheses after the names of the enzymes are the names of the genes coding for the respective enzymes (the same shall apply throughout this specification). Among these enzymes, aspartate semialdehyde dehydrogenase, aspartokinase I, homoserine kinase, aspartate aminotransferase, and threonine synthase can be enhanced. The genes coding for the L-threonine biosynthetic enzymes can be introduced into an *Escherichia* bacterium which has a reduced ability to decompose threonine. An example of such an *Escherichia* bacterium is the TDH6 strain which is deficient in threonine dehydrogenase activity (JP 2001-346578 A).

The enzymatic activities of the L-threonine biosynthetic enzymes can be inhibited by the endproduct, L-threonine. Therefore, the genes for the L-threonine biosynthetic enzymes can be modified so that the enzymes are desensitized to this feedback inhibition by L-threonine in the L-threonine-producing strains. The aforementioned thrA, thrB, and thrC genes constitute the threonine operon, which attenuates function. The expression of the threonine operon is inhibited by isoleucine and threonine in the culture medium and also suppressed by this attenuation. Therefore, the threonine operon can be modified by removing the leader sequence or the sequence responsible for attenuation in the attenuation region (refer to Lynn, S. P., Burton, W. S., Donohue, T. J., Gould, R. M., Gumport, R. I., and Gardner, J. F., J. Mol. Biol. 194:59-69 (1987); WO02/26993; WO2005/049808).

The native promoter of the threonine operon is present upstream of the threonine operon, and can be replaced with a non-native promoter (refer to WO98/04715), or a threonine operon which has been modified so that expression of the threonine biosynthesis gene is controlled by the repressor and promoter of λ-phage (EP 0593792). Furthermore, in order to modify a bacterium so it is desensitized to feedback inhibition by L-threonine, a strain resistant to α-amino-β-hydroxyisovaleric acid (AHV) can be selected.

The copy number can be increased of the threonine operon that is modified as described above so it is desensitized to feedback inhibition by L-threonine in the host bacterium, or the expression of such a modified operon can be increased by ligating it to a potent promoter. The copy number can also be increased by, besides amplification using a plasmid, transferring the threonine operon to a genome using a transposon, Mu-phage, or the like.

Other than increasing expression of the L-threonine biosynthetic genes, expression of the genes involved in the glycolytic pathway, TCA cycle, or respiratory chain, the genes that regulate the expression of these genes, or the genes involved in sugar uptake can also be increased. Examples of these genes include the genes encoding transhydrogenase (pntAB, EP 733712 B), phosphoenolpyruvate carboxylase (pepC, WO95/06114), phosphoenolpyruvate synthase (pps, EP 877090 B), and pyruvate carboxylase, all of which can be derived from coryneform bacterium or *Bacillus* bacterium (WO99/18228, EP 1092776 A).

Expression of genes that impart L-threonine resistance, L-homoserine resistance, and/or both to the host can also be enhanced. Examples of these genes include rhtA (Res. Microbiol., 154:123-135 (2003)), rhtB (EP 0994190 A), rhtC (EP 1013765 A), yfiK, and yeaS (EP 1016710 A). The methods for imparting L-threonine resistance to a host are described in EP 0994190 A and WO90/04636.

Examples of L-threonine-producing bacteria and parent strains which can be used to derive such bacteria include, but are not limited to, strains belonging to the genus *Escherichia*, such as *E. coli* TDH-6/pVIC40 (VKPM B-3996) (U.S. Pat. Nos. 5,175,107, 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A) and so forth.

The TDH-6 strain is deficient in the thrC gene, as well as being sucrose-assimilative, and the ilvA gene has a leaky mutation. This strain also has a mutation in the rhtA gene, which imparts resistance to high concentrations of threonine or homoserine. The B-3996 strain contains the plasmid pVIC40, which was obtained by inserting the thrA*BC operon, including a mutant thrA gene, into the RSF1010-derived vector. This mutant thrA gene encodes aspartokinase homoserine dehydrogenase I which is substantially desensitized to feedback inhibition by threonine. The B-3996 strain was deposited on Nov. 19, 1987 in the All-Union Scientific Center of Antibiotics (Nagatinskaya Street 3-A, 117105 Moscow, Russia) under the accession number RIA 1867. The strain was also deposited at the Russian National Collection of Industrial Microorganisms (VKPM) (1 Dorozhny proezd., 1 Moscow 117545, Russia) on Apr. 7, 1987 under the accession number VKPM B-3996.

*E. coli* VKPM B-5318 (EP 0593792 B) is also an L-threonine-producing bacterium. The B-5318 strain is prototrophic with regard to isoleucine, and a temperature-sensitive lambda-phage C1 repressor and PR promoter replace the regulatory region of the threonine operon in pVIC40. The VKPM B-5318 strain was deposited at the Russian National Collection of Industrial Microorganisms (VKPM) (1 Dorozhny proezd., 1 Moscow 117545, Russia) on May 3, 1990 under the accession number of VKPM B-5318.

The thrA gene which encodes aspartokinase homoserine dehydrogenase I of *Escherichia coli* has been elucidated (nucleotide positions 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession NC 000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession NC 000913.2, gi: 49175990). The thrC gene is located between the thrB gene and the yaaX open reading frame on the chromosome of *E. coli* K-12. All three genes function as a single threonine operon. To enhance expression of the threonine operon, the attenuator region which affects the transcription is desirably removed (WO2005/049808, WO2003/097839).

A mutant thrA gene which codes for aspartokinase homoserine dehydrogenase I resistant to feedback inhibition by threonine, as well as the thrB and thrC genes can be obtained as one operon from the well-known pVIC40 plasmid, which is present in the threonine-producing *E. coli* strain VKPM B-3996. pVIC40 is described in detail in U.S. Pat. No. 5,705,371.

The rhtA gene is present at 18 min on the *E. coli* chromosome, which is close to the glnHPQ operon, and which encodes components of the glutamine transport system. The rhtA gene is identical to ORF1 (ybiF gene, nucleotide numbers 764 to 1651, GenBank accession number AAA218541, gi: 440181) and is located between the pexB and ompX genes. The unit expressing the protein encoded by the ORP1 has been designated the rhtA gene (rht: resistance to homoserine and threonine). Also, it was revealed that the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide numbers 3572511 to 3571408, GenBank accession NC_000913.1, gi: 16131307), and can be obtained by PCR (polymerase chain reaction; refer to White, T. J. et al., Trends Genet, 5, 185 (1989)) utilizing primers prepared based on the nucleotide sequence of the gene. The asd genes of other microorganisms can also be obtained in a similar manner.

Also, the aspC gene of *E. coli* has already been elucidated (nucleotide numbers 983742 to 984932, GenBank accession NC 000913.1, gi: 16128895), and can be obtained by PCR. The aspC genes of other microorganisms can also be obtained in a similar manner.

L-Lysine-Producing Bacteria

Examples of L-lysine-producing bacteria belonging to the genus *Escherichia* include mutants having resistance to an L-lysine analogue. L-lysine analogues inhibit the growth of *Escherichia* bacteria, but this inhibition is fully or partially desensitized when L-lysine is present in the medium. Examples of these L-lysine analogues include, but are not limited to, oxalysine, lysine hydroxamate, S-(2-aminoethyl)-L-cysteine (AEC), γ-methyllysine, α-chlorocaprolactam, and so forth. Mutants having resistance to these lysine analogues can be obtained by subjecting *Escherichia* bacteria to conventional artificial mutagenesis treatments. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The WC1-96 strain is an L-lysine-producing *Escherichia coli*. This bacterial strain was bred from the W3110 strain, which was derived from *Escherichia coli* K-12, by replacing the lysC gene on the chromosome of the W3110 strain with a mutant lysC gene encoding a mutant aspartokinase III in which threonine at position 352 had been replaced with isoleucine (U.S. Pat. No. 5,661,012), and conferring AEC resistance to the resulting strain. The mutant aspartokinase III is not subject to feedback inhibition by L-lysine. The WC1-96 strain was designated *Escherichia coli* AJ13069 and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of L-lysine-producing bacteria and parent strains which can be used to derive L-lysine-producing bacteria also include strains in which expression of one or more genes encoding an L-lysine biosynthetic enzyme are enhanced. Examples of such enzymes include, but are not limited to, dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), diaminopimelate epimerase (dapF), tetrahydrodipicolinate succinylase (dapD), succinyl diaminopimelate deacylase (dapE), and aspartase (aspA) (EP 1253195 A). Among these enzymes, dihydrodipicolinate reductase, diaminopimelate decarboxylase, diaminopimelate dehydrogenase, phosphoenolpyrvate carboxylase, aspartate aminotransferase, diaminopimelate epimerase, aspartate semialdehyde dehydrogenease, tetrahydrodipicolinate succinylase, and succinyl diaminopimelate deacylase can be used. In addition, the parent strains may express increased levels of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), the gene encoding glutamate dehydrogenase (gdhA) (Gene, 23:199-209 (1983)) or combinations thereof.

Examples of L-lysine-producing bacteria and parent strains which can be used to derive L-lysine-producing bacteria also include strains in which the activity of one or more enzymes that catalyze one or more reactions which direct synthesis of one or more compounds other than L-lysine, for example, by directing synthesis away from the biosynthetic pathway of L-lysine, is reduced or eliminated. Examples of these enzymes include homoserine dehydrogenase, lysine decarboxylase (U.S. Pat. No. 5,827,698), and the malic enzyme (WO2005/010175).

An example of an L-lysine producing strain is *E. coli* WC196ΔcadAΔldc/pCABD2 (WO2006/078039). This strain was obtained by introducing the pCABD2 plasmid (U.S. Pat. No. 6,040,160) into the WC196 strain, in which the cadA and ldcC genes coding for lysine decarboxylase are disrupted. The pCABD2 plasmid contains the dapA gene derived from *Escherichia coli*, which has been mutated to encode dihydrodipicolinate synthase (DDPS) which is desensitized to the feedback inhibition by L-lysine, the lysC gene derived from *Escherichia coli*, which has been mutated to encode aspartokinase III which is desensitized to feedback inhibition by L-lysine, the dapB gene derived from *Escherichia coli* coding for dihydrodipicolinate reductase, and the ddh gene derived from *Brevibacterium lactofermentum* coding for diaminopimelate dehydrogenase.

L-Cysteine-Producing Bacteria

Examples of L-cysteine-producing bacteria and parent strains which can be used to derive L-cysteine-producing bacteria include, but are not limited to, *Escherichia* bacteria strains, such as *E. coli* JM15 which is transformed with different cysE alleles coding for feedback-resistant serine acetyltransferases (U.S. Pat. No. 6,218,168, Russian patent application 2003121601), *E. coli* W3110 which over-expresses genes encoding proteins which direct the secretion of substances which are toxic to cells (U.S. Pat. No. 5,972,663), *E. coli* strains with reduced cysteine desulfohydrase activity (JP 11155571 A2), *E. coli* W3110 with increased activity of a positive transcriptional regulator for the cysteine regulon encoded by the cysB gene (WO01/27307A1), and so forth.

L-Leucine-Producing Bacteria

Examples of L-leucine-producing bacteria and parent strains which can be used to derive L-leucine-producing bacteria include, but are not limited to, *Escherichia* bacterial strains, such as *E. coli* strains resistant to leucine (for example, the 57 strain (VKPM B-7386, U.S. Pat. No. 6,124,121)) or leucine analogues including β-2-thienylalanine, 3-hydroxyleucine, 4-azaleucine, 5,5,5-trifluoroleucine, and so forth (JP 62-34397 B and JP 8-70879 A), *E. coli* strains obtained by the genetic engineering method described in WO96/06926, *E. coli* H-9068 (JP 8-70879 A), and so forth.

The bacterium may be improved by enhancing expression of one or more genes involved in L-leucine biosynthesis. Examples of such genes include the genes of the leuABCD operon, a typical example of which is the leuA gene coding for isopropyl malate synthase which has been mutated to be desensitized to feedback inhibition by L-leucine (U.S. Pat. No. 6,403,342). In addition, the bacterium may be improved by enhancing expression of one or more genes coding for proteins which increase the secretion of L-amino acid from the bacterial cell. Examples of such genes include b2682 and b2683 (the ygaZH genes) (EP 1239041 A2).

L-Histidine-Producing Bacteria

Examples of L-histidine-producing bacteria and parent strains which can be used to derive L-histidine-producing bacteria include, but are not limited to, *Escherichia* bacterial strains, such as *E. coli* strain 24 (VKPM B-5945, RU2003677), *E. coli* strain 80 (VKPM B-7270, RU2119536), *E. coli* NRRL B-12116-B 12121 (U.S. Pat. No. 4,388,405), *E. coli* H-9342 (FERM BP-6675), *E. coli* H-9343 (FERM BP-6676) (U.S. Pat. No. 6,344,347), *E. coli* H-9341 (FERM BP-6674) (EP 1085087), *E. coli* AI80/pFM201 (U.S. Pat. No. 6,258,554), and so forth.

Examples of L-histidine-producing bacteria and parent strains which can be used to derive L-histidine-producing bacteria also include strains in which the expression of one or more genes encoding L-histidine biosynthetic enzymes is enhanced. Examples of such genes include the genes encoding ATP phosphoribosyltransferase (hisG), phosphoribosyl AMP cyclohydrolase (hisI), phosphoribosyl-ATP pyrophosphohydrolase (hisE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore the ability to produce L-histidine can also be efficiently enhanced by introducing a mutation which confers resistance to feedback inhibition into the gene coding for ATP phosphoribosyltransferase (hisG) (Russian Patent Nos. 2003677 and 2119536).

Specific examples of strains which are able to produce L-histidine include E. coli FERM-P 5038 and 5048 which have been transformed with a vector carrying a DNA encoding an L-histidine-biosynthetic enzyme (JP 56-005099 A), E. coli strains transformed with a gene encoding a protein involved in amino acid export (EP 1016710 A), E. coli 80 strain which is resistant to sulfaguanidine, DL-1,2,4-triazole-3-alanine, and streptomycin (VKPM B-7270, Russian Patent No. 2119536), and so forth.

L-Glutamic Acid-Producing Bacteria

Examples of L-glutamic acid-producing bacteria and parent strains which can be used to derive L-glutamic acid-producing bacteria include, but are not limited to, *Escherichia* bacterial strains, such as *E. coli* VL334thrC$^+$ (EP 1172433). *E. coli* VL334 (VKPM B-1641) is auxotrophic for L-isoleucine and L-threonine and contains mutant thrC and ilvA genes (U.S. Pat. No. 4,278,765). A wild-type allele of the thrC gene was transferred by general transduction using bacteriophage P1 grown on wild-type *E. coli* K12 (VKPM B-7) cells, resulting in a strain, which is able to produce L-glutamic acid. This strain was named VL334thrC$^+$ (VKPM B-8961). Examples of L-glutamic acid-producing bacteria and parent strains which can be used to derive L-glutamic acid-producing bacteria include, but are not limited to, strains in which expression of one or more genes encoding an L-glutamic acid biosynthetic enzyme is enhanced. Examples of such genes include the genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), methyl citrate synthase gene (prpC), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), and so forth. Among these enzymes, glutamate dehydrogenase, citrate synthase, phosphoenolpyruvate carboxylase, and methyl citrate synthase can be used.

Examples of strains which have been modified so that expression of the citrate synthetase gene, the phosphoenolpyruvate carboxylase gene, and/or the glutamate dehydrogenase gene is enhanced include those disclosed in EP 1078989 A, EP 955368 A, and EP 952221A.

Examples of L-glutamic acid-producing bacteria and parent strains which can be used to derive L-glutamic acid-producing bacteria also include strains in which the activity of one or more enzymes that catalyze one or more reactions which direct synthesis of one or more compounds other than L-glutamic acid, for example, by directing synthesis away from the biosynthetic pathway of L-glutamic acid, is reduced or eliminated. Examples of these enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), glutamate decarboxylase (gadAB), and so forth. *Escherichia* bacteria without α-ketoglutarate dehydrogenase activity or with reduced α-ketoglutarate dehydrogenase activity and methods to obtain such bacteria are described in U.S. Pat. Nos. 5,378,616 and 5,573,945.

Specifically, these strains include the following:
*E. coli* W3110sucA::Km$^r$
*E. coli* AJ12624 (FERM BP-3853)
*E. coli* AJ12628 (FERM BP-3854)
*E. coli* AJ12949 (FERM BP-4881)

*E. coli* W3110sucA::Km$^r$ is obtained by disrupting the α-ketoglutarate dehydrogenase gene (hereinafter also referred to as the "sucA gene") of *E. coli* W3110. This strain is completely deficient in α-ketoglutarate dehydrogenase.

Other examples of L-glutamic acid-producing bacterium include *Escherichia* bacteria which are resistant to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FFRM P-12379, which additionally is unable to decompose L-glutamic acid (U.S. Pat. No. 5,393,671); AJ13138 (FERM BP-5565) (U.S. Pat. No. 6,110,714), and so forth.

An example of an L-glutamic acid-producing bacterium which belongs to the genus *Pantoea ananatis* is, but is not limited to, the *Pantoea ananatis* AJ13355 strain. This strain was isolated from soil in Iwata-shi, Shizuoka-ken, Japan, and was identified as being able to proliferate in a medium containing L-glutamic acid and a carbon source at a low pH. The *Pantoea ananatis* AJ13355 strain was deposited at the National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Feb. 19, 1998 and received an accession number of FERM P-16644. It was then converted to an international deposit under the provisions of Budapest Treaty on Jan. 11, 1999 and received an accession number of FERM BP-6614. This strain was originally identified as *Enterobacter agglomerans* when it was isolated, and deposited as *Enterobacter agglomerans* AJ13355. However, it was recently re-classified as *Pantoea ananatis* on the basis of nucleotide sequencing of 16S rRNA and so forth.

Furthermore, the α-ketoglutarate dehydrogenase (αKGDH) activity can be eliminated or reduced in bacteria belonging to the genus *Pantoea*. Examples of such a strain include AJ13356 (U.S. Pat. No. 6,331,419), which was derived by deleting the αKGDH-E1 subunit gene (sucA) in AJ13355, and the SC17sucA strain (U.S. Pat. No. 6,596,517) which also does not have the sucA gene, and was selected from AJ13355 for its low phlegm production properties. The AJ13356 strain was deposited at the National Institute of Bioscience and Human-Technology, Agency of Industrial Science and Technology, Ministry of International Trade and Industry (currently, the independent administrative agency, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566)) on Feb. 19, 1998, and assigned an accession number of FERM P-16645. Then, the deposit was converted into an international deposit under the provisions of the Budapest Treaty on Jan. 11, 1999, and assigned an accession number of FERM BP-6616. Although the AJ13355 and AJ13356 strains were deposited at the aforementioned depository as *Enterobacter agglomerans*, they are referred to as *Pantoea ananatis* in this specification. The SC17sucA strain was assigned the private number of AJ417, and deposited at the National Institute of Advanced Industrial Science and Technology, International Patent Organism Depositary on Feb. 26, 2004, under an accession number of FERM BP-08646.

Examples of L-glutamic acid-producing *Pantoea ananatis* bacteria further include SC17sucA/RSFCPG+pSTVCB, AJ13601, NP106, and NA1. The SC17sucA/RSFCPG+pSTVCB strain was obtained by introducing the plasmid RSFCPG containing the citrate synthase gene (gltA), phosphoenolpyruvate carboxylase gene (ppsA), and glutamate dehydrogenase gene (gdhA) derived from *Escherichia coli*, and the plasmid pSTVCB containing the citrate synthase gene (gltA) derived from *Brevibacterium lactofermentum*, into the SC17sucA strain. The AJ13601 strain was selected from the SC17sucA/RSFCPG+pSTVCB strain for its resistance to high concentrations of L-glutamic acid at a low pH. Furthermore, the NP106 strain was derived from the AJ13601 strain by eliminating the RSFCPG+pSTVCB plasmid as described in the examples. The AJ13601 strain was deposited at the National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566) on Aug. 18, 1999, and assigned accession number FERM P-17516. Then, the deposit was converted into an international deposit under the provisions of the Budapest Treaty on Jul. 6, 2000, and assigned an accession number FERM BP-7207.

L-Phenylalanine-Producing Bacteria

Examples of L-phenylalanine-producing bacteria and parent strains which can be used to derive L-phenylalanine-producing bacteria include, but are not limited to, *Escherichia* bacterial strains, such as *E. coli* AJ12739 (tyrA::Tn10, tyrR) (VKPM B-8197) which lacks chorismate mutase-prephenate dehydrogenase and the tyrosine repressor (WO03/044191), *E. coli* HW1089 (ATCC 55371) which contains the pheA34 gene coding for chorismate mutase-prephenate dehydratase which has been mutated to be desensitized to feedback inhibition (U.S. Pat. No. 5,354,672), *E. coli* MWEC101-b (KR8903681), *E. coli* NRRL B-12141, NRRL B-12145, NRRL B-12146, and NRRL B-12147 (U.S. Pat. No. 4,407, 952). Also, the following strains can be used to derive L-phenylalanine producing bacteria: *E. coli* K-12 [W3110(tyrA)/pPHAB (FERM BP-3566) which contains genes coding for chorismate mutase-prephenate dehydratase which has beem mutated to be desensitized to feedback inhibition, *E. coli* K-12 [W3110(tyrA)/pPHAD] (FERM BP-12659), *E. coli* K-12 [W3110(tyrA)/pPHATerm] (FERM BP-12662), and *E. coli* K-12 [W3110(tyrA)/pBR-aroG4, pACMAB] (also known as AJ12604 (FERM BP-3579) (EP 488-424 B1). Furthermore, *Escherichia* L-phenylalanine-producing bacteria with enhanced activity of the protein encoded by the yedA gene or the yddG gene may also be used (U.S. Patent Published Applications Nos. 2003/0148473 A1 and 2003/0157667 A1, WO03/044192).

L-Tryptophan-Producing Bacteria

Examples of L-tryptophan-producing bacteria and parent strains which can be used to derive L-tryptophan-producing bacteria include, but are not limited to, *Escherichia* bacterial strains, such as *E. coli* JP4735/pMU3028 (DSM10122), *E. coli* JP6015/pMU91 (DSM10123) which lacks tryptophanyl-tRNA synthetase encoded by a mutant trpS gene (U.S. Pat. No. 5,756,345), *E. coli* SV164 (pGH5) which contains the serA allele encoding phosphoglycerate dehydrogenase and the trpE allele encoding anthranilate synthase, both of which are not subject to feedback inhibition by serine and tryptophan, respectively (U.S. Pat. No. 6,180,373), *E. coli* AGX17 (pGX44) (NRRL B-12263), *E. coli* AGX6(pGX50) aroP (NRRL B-12264) which lacks tryptophanase (U.S. Pat. No. 4,371,614), and *E. coli* AGX17/pGX50, pACKG4-pps in which phosphoenolpyruvate-producing ability is enhanced (WO9708333, U.S. Pat. No. 6,319,696). L-tryptophan-producing bacteria belonging to the genus *Escherichia* with enhanced activity of the protein encoded by the yedA gene or the yddG gene may also be used (U.S. Patent Published Application Nos. 2003/0148473 A1 and 2003/0157667 A1).

Examples of L-tryptophan-producing bacteria and parent strains which can be used to derive L-tryptophan-producing bacteria also include strains in which one or more activities of the following enzymes are enhanced: anthranilate synthase (trpE), phosphoglycerate dehydrogenase (serA), 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), chorismate synthase (aroC), prephenate dehydratase, chorismate mutase, and tryptophan synthase (trpAB). Prephenate dehydratase and chorismate mutase are encoded by the pheA gene as a bifunctional enzyme (CM-PD). Among these enzymes, phosphoglycerate dehydrogenase, 3-deoxy-D-arabinoheptulosonate-7-phosphate synthase, 3-dehydroquinate synthase, shikimate dehydratase, shikimate kinase, 5-enolpyruvylshikimate-3-phosphate synthase, chorismate synthase, prephenate dehydratase, and chorismate mutase-prephenate dehydratase can be used. Anthranilate synthase and phosphoglycerate dehydrogenase both suffer from feedback inhibition by L-tryptophan and L-serine, and therefore a mutation desensitizing feedback inhibition may be introduced into the genes encoding these enzymes. Specific examples of strains having such a mutation include *E. coli* SV164 and a transformant strain obtained by introducing pGH5 (WO94/08031) into SV164, resulting in feedback-desensitized phosphoglycerate dehydrogenase due to a mutant serA gene.

Examples of L-tryptophan-producing bacteria and parent strains which can be used to derive L-tryptophan-producing bacteria also include strains which have been transformed with the tryptophan operon, which contains a gene encoding inhibition-desensitized anthranilate synthase (JP 57-71397 A, JP 62-244382 A, U.S. Pat. No. 4,371,614). Moreover, L-tryptophan-producing ability may be imparted by enhancing expression of a gene which encodes tryptophan synthase, also on the tryptophan operon (trpBA). Tryptophan synthase includes both α and β subunits, which are encoded by trpA and trpB, respectively. In addition, L-tryptophan-producing ability may be improved by enhancing expression of the isocitrate lyase-malate synthase operon (WO2005/103275).

L-Proline-Producing Bacteria

Examples of L-proline-producing bacteria and parent strains which can be used to derive L-proline-producing bacteria include, but are not limited to, *Escherichia* bacterial strains, such as *E. coli* 702ilvA (VKPM B-8012) which lacks the ilvA gene (EP 1172433).

The bacterium may be improved by enhancing expression of one or more genes involved in L-proline biosynthesis. Examples of such genes include the proB gene coding for glutamate kinase which is desensitized to feedback inhibition by L-proline (DE Patent 3127361). In addition, the bacterium may be improved by enhancing expression of one or more genes coding for proteins responsible for secretion of L-amino acids from the bacterial cell. Examples of such genes are b2682 and b2683 (ygaZH genes) (EP 1239041 A2).

*Escherichia* bacteria which produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15th Miami Winter Symposium, 1983, p. 34), and so forth.

L-Arginine-Producing Bacteria

Examples of L-arginine-producing bacteria and parent strains which can be used to derive L-arginine-producing bacteria include, but are not limited to, *Escherichia* bacterial strains, such as *E. coli* strain 237 (VKPM B-7925) (U.S. Patent Published Application No. 2002/058315 A1) and its derivative strains harboring mutant N-acetylglutamate synthase (Russian Patent Application No. 2001112869), *E. coli* strain 382 (VKPM B-7926) (EP 1170358A1), and an arginine-producing strain transformed with an argA gene encoding N-acetylglutamate synthetase (EP 1170361 A1).

Examples of L-arginine-producing bacteria and parent strains which can be used to derive L-arginine-producing bacteria also include strains in which the expression of one or more genes encoding an L-arginine biosynthetic enzyme is enhanced. Examples of such genes include the genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Examples of L-valine-producing bacteria and parent strains which can be used to derive L-valine-producing bacteria include, but are not limited to, strains which have been modified to overexpress the ilvGMEDA operon (U.S. Pat. No. 5,998,178). It is desirable to remove the region in the ilvGMEDA operon which is required for attenuation so that expression of the operon is not attenuated by the produced L-valine. Furthermore, the ilvA gene in the operon is desirably disrupted so that threonine deaminase activity is decreased.

Examples of L-valine-producing bacteria and parent strains which can be used to derive L-valine-producing bacteria also include mutants having amino-acyl t-RNA synthetase mutations (U.S. Pat. No. 5,658,766). An example is *E. coli* VL1970, which has a mutation in the ileS gene encoding isoleucine tRNA synthetase. *E. coli* VL1970 was deposited at the Russian National Collection of Industrial Microorganisms (VKPM) (1 Dorozhny proezd., 1 Moscow 117545, Russia) on Jun. 24, 1988 under the accession number VKPM B-4411.

Furthermore, mutant strains which require lipoic acid for growth and/or lacking $H^+$-ATPase are also effective to derive L-valine-producing bacteria (WO96/06926).

L-Isoleucine-Producing Bacteria

Examples of L-isoleucine producing bacteria and parent strains which can be used to derive L-isoleucine producing bacteria include, but are not limited to, mutants which are resistant to 6-dimethylaminopurine (JP 5-304969 A), mutants which are resistant to isoleucine analogues such as thiaisoleucine and isoleucine hydroxamate, and mutants which are additionally resistant to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, are also effective to derive L-isoleucine-producing bacteria (JP 2-458 A, FR 0356739, and U.S. Pat. No. 5,998,178).

L-Tyrosine-Producing Bacteria

Examples of tyrosine-producing bacteria include *Escherichia* bacteria with a desensitized prephenate dehydratase gene (tyrA). The expression product of this gene is desensitized to inhibition by tyrosine (European Patent Application Laid-open No. 1616940).

When the aforementioned L-amino acid-producing bacteria are bred by genetic recombination, the genes are not limited to the genes having the genetic information cited herein or genes having known sequences. Variants of these genes, that is, genes having conservative mutations such as homologues or artificially modified genes can also be used so long as the functions of the encoded proteins are not degraded. That is, genes are encompassed which encode variants of the known amino acid sequence, in that they may contain one or several substitutions, deletions, insertions, additions, or the like of one or several amino acid residues at one or several positions.

Although the number of the "several" amino acid residues referred to herein may differ depending on position of the object amino acid in the three-dimensional structure of the protein or the type of amino acid being mutated, specifically, it may be 1 to 20 in one example, 1 to 10 in another example, and 1 to 5 in yet another example. Conservative substitutions take place mutually among Phe, Trp and Tyr, if the substitution site is an aromatic amino acid; among Leu, Ile and Val, if it is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. Typical examples of conservative mutations are conservative substitutions, which include, specifically, substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. The aforementioned amino acid substitution, deletion, insertion, addition, inversion or the like may be a result of a naturally-occurring mutation or variation due to an individual difference or difference of species of a microorganism from which the genes are derived (mutant or variant). Such genes can be obtained by, for example, modifying the known nucleotide sequence of a gene by site-specific mutagenesis so that amino acid residues of specific sites of the encoded protein includes substitutions, deletions, insertions or additions of amino acid residues.

Furthermore, genes with conservative mutations as mentioned above may encode for a protein having a homology of 80% or more, 90% or more in another example, 95% or more in another example, 97% or more in another example, to the total encoded non-variant amino acid sequence, and having a function equivalent to that of the wild-type or non-variant protein.

Moreover, codons in the gene sequences may be replaced with codons which function better in the chosen host.

The genes with conservative mutations may be obtained by typical mutagenesis treatments, such as by treating with mutagenesis agents.

Furthermore, the genes may be DNA which can hybridize with the complementary sequence of the known gene sequence, or a probe which can be prepared from the complementary sequence, under stringent conditions and codes for a protein which has a function equivalent to that of the known gene product. The "stringent conditions" are those under which a so-called specific hybrid is formed, and a non-specific hybrid is not formed. Examples of the stringent conditions include those under which highly homologous DNAs hybridize to each other, for example, DNAs not less than 80% homologous, not less than 90% homologous in another example, not less than 95% homologous in another example, not less than 97% homologous in another example, hybridize to each other, and DNAs less homologous than the above do not hybridize to each other, or conditions of washing once, or 2 or 3 times, at a salt concentration and temperature corresponding to washing conditions typical of Southern hybridization, i.e., 1×SSC, 0.1% SDS at 60° C., 0.1×SSC, 0.1% SDS at 60° C. in another example, and 0.1×SSC, 0.1% SDS at 68° C. in another example.

As the probe, a part of the sequence complementary to the gene can also be used. Such a probe can be prepared by PCR using oligonucleotide primers prepared on the basis of the known gene sequence, and a DNA fragment containing the nucleotide sequences as the template. For example, when a DNA fragment having a length of about 300 by is used as the probe, the washing conditions of hybridization may be 50° C., 2×SSC and 0.1% SDS.

The above descriptions concerning variants of the genes are similarly applied to the rng gene described below.

<2-2> Decrease of Ribonuclease G Activity

The modification which is made to decrease the activity of ribonuclease G in an Enterobacteriaceae bacterium will be explained below.

"Ribonuclease G (RNase G) activity" includes the activity of decomposing the RNA which is the substrate of RNase G.

Examples of this substrate RNA include, for example, RNAs transcribed from the eno gene coding for enolase (GenBank Accession No. X82400), the adhE gene coding for alcohol dehydrogenase (GenBank Accession No. M33504), and so forth. The activity can be indirectly measured by, for example, extracting RNA from a strain in which RNA synthesis is suppressed by rifampicin, and measuring the decomposition half life of the mRNA of the eno or adhE gene. Moreover, the activity can also be measured by isolating and purifying RNase G, and using it to measure the digestion reaction of an artificial substrate, such as an oligoribonucleotide containing the RNase G digestion site (J. Biol. Chem., 275, 8726-8732, 2000). Such an activity measurement method is already disclosed.

The expression "modified so that RNase G activity is decreased" means that the RNase G activity per bacterial cell is lower than that of a non-modified strain, such as a wild-type strain of an Enterobacteriaceae bacterium. This includes, for example, when the molecular number of RNase G per cell decreases, when the RNase G specific activity per molecule decreases, and the like. The RNase G activity per cell can be compared with, for example, the RNase G activities from cell extracts of a culture performed under the same conditions. In addition, the "decrease" in activity can include the complete absence of activity. Examples of a wild-type *Escherichia* bacterium which may serve as a control for the above comparison include, for example, the *Escherichia coli* MG1655 strain, and so forth.

The decrease in RNase G activity can be attained by inactivation of the gene coding for RNase G (rng). The "inactivation" of the rng gene means modifying the gene by genetic recombination or introducing a mutation into the gene so that the RNase G activity encoded by the gene decreases or is absent.

Examples of the rng gene include the rng gene derived from or native to *Escherichia coli* registered at GenBank (complementary strand of the nucleotide numbers 3394348 to 3395817 of GenBank Accession No. NC_000913.2, SEQ ID NO: 1). The amino acid sequence of RNase G encoded by this rng gene is shown in SEQ ID NO: 2. The rng gene can be cloned by PCR using synthetic oligonucleotide primers synthesized on the basis of the aforementioned sequence and the *Escherichia coli* chromosome as the template. Moreover, when the rng gene is deleted by homologous recombination, a gene having a homology higher than a certain level, for example, 80% or more, 90% or more in another example, 95% or more in another example, to the rng gene on the chromosome can also be used. Furthermore, a gene which is able to hybridize with the rng gene on the chromosome under stringent conditions can also be used. Examples of the stringent conditions include, for example, washing once, or washing two or three times, at salt concentrations corresponding to 1×SSC and 0.1% SDS in one example, 0.1×SSC and 0.1% SDS in another example, at 60° C.

Specifically, the rng gene may be inactivated by, for example, deleting a part or the entire coding region of the rng gene on the chromosome, or inserting another sequence into the coding region. These techniques are also called gene disruption.

The rng gene can also be inactivated by decreasing expression of the rng gene by modifying an expression control sequence such as a promoter or Shine Dargarno (SD) sequence of the rng gene, or the like. Decrease in expression also includes a decrease in either transcription and/or translation. Expression of the gene can also be decreased by modifying other non-translated regions other than the expression control regions.

Furthermore, the entire target gene including the upstream and downstream regions of the gene on the chromosome may be deleted. In addition, the rng gene can also be inactivated by introducing a mutation which results in an amino acid substitution (missense mutation), a stop codon (nonsense mutation), or a frame shift which adds or deletes one or two nucleotides in the coding region of the rng gene on the chromosome (Journal of Biological Chemistry, 272:8611-8617 (1997); Proceedings of the National Academy of Sciences, USA, 95 5511-5515 (1998); Journal of Biological Chemistry, 266, 20833-20839 (1991)).

The gene can be modified by genetic recombination. Specific examples of genetic recombination methods include the deletion of part of, or the entire, expression control sequence of the target gene on the chromosome, for example, the promoter region, or a coding or non-coding region, and insertion of another sequence into these regions.

One or more nucleotides can be modified in the expression control sequence, two or more nucleotides can be modified in another example, and three or more nucleotides can be modified in another example. When a coding region is deleted, it may be an N-terminus region, an internal region, or a C-terminus region, or even the entire coding region, so long as the function of the protein produced by the gene is reduced or deleted. The longer the deleted region, the more likely the target gene will be inactivated. Furthermore, the reading frames upstream and downstream of the deleted region should not be the same.

When another sequence is inserted into the coding region, it may be inserted into any region of the target gene, and the longer the inserted sequence, the more likely the target gene will be inactivated. The reading frames upstream and downstream of the inserted region should not be the same. The sequence to be inserted is not particularly limited so long as it results in a reduction or deletion of function of the protein encoded by the target gene, and examples include, for example, a transposon carrying an antibiotic resistance gene or a gene useful for L-amino acid production.

The target gene on the chromosome can be modified as described above by, for example, preparing the gene so that it is missing a partial sequence and, as a result, cannot produce a protein that functions normally, and transforming a bacterium with DNA containing the disrupted gene to cause homologous recombination between the disrupted gene and the native gene on the chromosome, resulting in substitution of the native gene on the chromosome with the disrupted gene. The protein encoded by the disrupted gene will have a conformation different from that of the wild-type protein, if it is even produced, and thus the function is reduced or absent. Such gene disruption based on gene substitution utilizing homologous recombination has been already established, and methods utilizing these techniques include the method of Red driven integration (Datsenko, K. A, and Wanner, B. L., Proc. Natl. Acad. Sci. USA, 97:6640-6645 (2000)), the method of using a linear DNA such as by utilizing the Red driven integration in combination with an excision system derived from phage (Cho, E. H., Gumport, R. I., Gardner, J. F., J. Bacteriol., 184:5200-5203 (2002)), the method of using a plasmid containing a temperature sensitive replication origin or a plasmid capable of conjugative transfer, the method of utilizing a suicide vector not having a replication origin in the chosen host (U.S. Pat. No. 6,303,383, JP 05-007491 A), and so forth.

The decrease in transcription of the target gene can be confirmed by comparing the amount of mRNA transcribed from the target gene with that in the wild-type or non-modified strain. Methods for measuring mRNA include, for example, Northern hybridization, RT-PCR, and so forth (Molecular Cloning, Cold spring Harbor Laboratory Press, Cold Spring Harbor (USA), 2001). Although the decrease in transcription may be to any extent so long as it decreases as compared to that observed in the wild-type or non-modified strain, it can be decreased at least by 75% or less, 50% or less, 25% or less, or 10% or less, and the gene may not be expressed at all.

The decrease in the amount of a protein encoded by the target gene can be confirmed by Western blotting using antibodies that bind to the protein (Molecular Cloning, Cold Spring Harbor Laboratory Press, Cold Spring Harbor (USA) 2001). Although the decrease in the amount of the protein may be to any extent so long as it decreases as compared to that observed in the wild-type or non-modified strain, it can be decreased by at least 75% or less, 50% or less, 25% or less, or 10% or less, and the protein may not be produced at all (the activity is completely absent).

Furthermore, the gene coding for a low activity RNase G can also be obtained by subjecting the rng gene to a mutation treatment. For example, since expression of the adhE gene coding for alcohol dehydrogenase depends on the function of the rng gene (Biochem. Biophys. Res. Commun., 295 (2002) 92-97), one can screen for a rng gene which is not expressed or expresses a low-activity RNase G by using a cell which contains a plasmid ligated with a promoter of adhE and a reporter gene such as the β-galactosidase gene and the suspect mutant rng gene, and measuring the β-galactosidase activity.

Examples of the method for decreasing the activity of RNase G include, besides the aforementioned genetic manipulation techniques, for example, treating an *Escherichia* bacterium with ultraviolet irradiation or a known mutagen such as N-methyl-N'-nitro-N-nitrosoguanidine (NTG) or nitrous acid, and selecting a strain with decreased RNase G activity. Examples of such a mutant strain with decreased RNase G activity include a strain in which only the activity for decomposing mRNA is reduced while the activity for maturing the 5' end of 16S rRNA is maintained, for example, the DC430 strain, GM1430 strain (Biochem. Biophys. Res. Commun., 289 (5), 1301-1306, 201), and so forth.

<3> Method for Producing L-Amino Acid

The method for producing an L-amino acid includes culturing an Enterobacteriaceae bacterium having an L-amino acid-producing ability which has been modified so that RNase G activity is decreased in a medium containing glycerol as the carbon source, and the L-amino acid is collected from the culture.

The glycerol concentration may be any concentration so long as it is suitable for production of the desired L-amino acid. When glycerol is used as the sole carbon source in the medium, it can be present in the medium in an amount of about 0.1 to 50 w/v %, about 0.5 to 40 w/v % in another example, or about 1 to 30% w/v % in another example. Glycerol can also be used in combination with other carbon sources such as glucose, fructose, sucrose, blackstrap molasses, and starch hydrolysate. In this case, although glycerol and other carbon sources may be mixed at an arbitrary ratio, the ratio of glycerol in the carbon source can be 10% by weight or more, 50% by weight or more in another example, or 70% by weight or more in another example. Other carbon sources include saccharides such as glucose, fructose, sucrose, lactose, galactose, blackstrap molasses, starch hydrolysate and a sugar solution obtained by hydrolysis of biomass, alcohols such as ethanol, and organic acids such as fumaric acid, citric acid and succinic acid. Among these, glucose can be used. A mixture containing crude glycerol and glucose at a weight ratio of 50:50 to 90:10 can also be used.

Although the initial concentration of glycerol at the start of the culture is as described above, glycerol may be supplemented as it is consumed during the culture.

Crude glycerol can be added to the medium. Crude glycerol can be added to the medium so it is at a concentration within the aforementioned range depending on purity of the glycerol.

Furthermore, both glycerol and crude glycerol can be added to the medium.

Media conventionally used in the production of L-amino acids by fermentation using microorganisms can be used. That is, typical media may contain, besides a carbon source, a nitrogen source, inorganic ions, and optionally other organic components as required. As the nitrogen source, inorganic ammonium salts such as ammonium sulfate, ammonium chloride, and ammonium phosphate, organic nitrogen such as soybean hydrolysate, ammonia gas, aqueous ammonia, and so forth may be used. As for organic trace nutrient sources, the medium can contain required substances such as vitamin $B_1$ and L-homoserine or yeast extract or the like in appropriate amounts. Other than the above, potassium phosphate, magnesium sulfate, iron ions, manganese ions and so forth can be added in small amounts, as required. In addition, the medium may be either natural or synthetic, so long as it contains a carbon source, a nitrogen source, inorganic ions, and other organic trace components as required.

EXAMPLES

Hereinafter, the present invention will be more specifically explained with reference to the following non-limiting examples.

Example 1

Construction of L-Lysine-Producing Bacterium Having Decreased Ribonuclease G Activity <1-2> Construction of a Strain which does not Express Ribonuclease G (rng Gene-Deficient Strain, WC196ΔcadAΔldcCΔrng Strain) from the WC196ΔcadAΔldcC Strain The WC196ΔcadAΔldcC strain is able to produce L-lysine and was used to derive the objective rng gene-deficient strain. The rng gene in WC196ΔcadAΔldcC was deleted by the method called "Red-driven integration", which was first developed by Datsenko and Wanner (Proc. Natl. Acad. Sci. USA., 2000, vol. 97, No. 12, pp. 6640-6645), and the excision system derived from λ phage (Cho E. H., Gumport R. I., and Gardner J. F., J. Bacteriol., 2002 Sep., 184 (18):5200-3, Interactions between integrase and excisionase in the phage lambda excisive nucleoprotein complex). By the "Red-driven integration" method, a gene-disrupted strain can be constructed in one step using a PCR product obtained by using synthetic oligonucleotide primers designed so as to contain a part of the objective gene on the 5' end and a part of an antibiotic resistance gene on the 3' end, respectively. By then using the excision system derived from phage, the antibiotic resistance gene which was integrated into the gene-disrupted strain can be eliminated.

The rng gene can be deleted by using the primers of SEQ ID NOS: 3 and 4 as primers. The WC196ΔcadAΔldcCΔrng::Cm strain, in which the ribonuclease G gene is deleted, was thereby obtained. The cadA gene and the ldcC gene in the WC196196ΔcadAΔldcC strain may also be deleted in a similar manner.

The WC196ΔcadAΔldcC and WC196ΔcadAΔldcCΔrng::Cm strains were transformed in a conventional manner with the plasmid pCABD2 which carries the dapA, dapB, and lysC genes (International Patent Publication WO01/53459) to obtain the WC196ΔcadAΔldcC/pCABD2 and WC196ΔcadAΔldcCΔrng::Cm/pCABD2, respectively. Furthermore, each strain was cultured at 37° C. in L medium containing 20 mg/L of streptomycin until the final OD600 of the culture became about 0.6. Then, an equal volume of a 40% glycerol solution was added to the culture, the mixture was stirred, and then divided into appropriate volumes and stored at −80° C. These are called glycerol stocks.

Example 2

Evaluation of L-Lysine Producing Ability of the Strain which does Not Express Ribonuclease G Each of the glycerol stocks of the strains was thawed, and 100 μL of each was evenly applied to an L plate containing 20 mg/L of streptomycin, and cultured at 37° C. for 24 hours. Then, ⅛ of the cells on the plate were inoculated into 20 mL of a fermentation medium containing 20 mg/L of streptomycin in a 500-mL Sakaguchi flask, and cultured at 37° C. for 24 hours while stirring at 115 rpm in a reciprocal shaker. After the culture, the amount of L-lysine which accumulated in the medium was measured by a known method (Biotec Analyzer AS210, SAKURA SEIKI).

The composition of the fermentation medium is shown below (unit: g/L).

Composition of L-Lysine Fermentation Medium:

| | |
|---|---|
| Glucose or glycerol | 40 |
| $(NH_4)_2SO_4$ | 24 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Yeast extract | 2.0 |
| $CaCO_3$ (Japanese Pharmacopoeia) | 30 |
| Distilled water | To final volume of 1 L |

The medium was adjusted to pH 7.0 with KOH, and autoclaved at 115° C. for 10 minutes. The glucose or glycerol and $MgSO_4 \cdot 7H_2O$ were sterilized separately, and $CaCO_3$ was subjected to hot air sterilization at 180° C. for 2 hours.

As an antibiotic, 20 mg/L of streptomycin was added.

The results are shown in Table 1. The yield (%) represents the yield of L-lysine based on glucose or glycerol. As seen from the results shown in Table 1, the WC196ΔcadAΔldcCΔrng::Cm/pCABD2 strain was able to produce L-lysine in a larger amount as compared to that observed for the WC196ΔcadAΔldcC/pCABD2 strain, in which the rng gene was not deleted.

TABLE 1

| | Yield (%) | |
|---|---|---|
| | Glucose | Glycerol |
| WC196ΔcadAΔldcC/pCABD2 | 41.5 | 40.0 |
| WC196ΔcadAΔldcCΔrng::Cm/pCABD2 | 42.6 | 43.9 |

Example 3

Construction of L-Threonine-Producing Strain Having Decreased Ribonuclease G Activity and Production of L-Threonine <3-1> Construction of Strains which do not Produce Ribonuclease G from L-Threonine-Producing *Escherichia coli* Strain B-5318

A strain which does not produce ribonuclease G was constructed from the threonine-producing bacterium, the B-5318 strain (*E. coli* VKPM B-5318) using primers of SEQ ID NOS: 3 and 4 for deleting the rng gene. Thus, a strain which does not produce ribonuclease G, B-5318Δrng::Tet was constructed.

The B-5318Δ::Tet strain was cultured at 37° C. in the L medium containing 20 mg/L of streptomycin until final OD600 of the culture became about 0.6. Then, an equal volume of a 40% glycerol solution was added to the culture, and the mixture was stirred, then divided into appropriate volumes and stored at −80° C. These are called glycerol stock. Each of the glycerol stocks of the B-5318 strain and the B-5318Δ::Tet strain was thawed, and evenly applied in a volume of 100 μL on an L plate containing 20 mg/L of streptomycin, and culture was performed at 37° C. for 24 hours. The cells on the plate were suspended in 1 ml of physiological saline. The cell suspension of a volume (V) was inoculated into 20 mL of a fermentation medium containing 20 mg/L of streptomycin contained in a 500-mL baffle flask, and cultured at 40° C. for 24 hours in a rotary shaker at 144 rpm. The volume (V) was calculated by dividing the constant 50 by $OD_{600}$ value (n) of a cell suspension diluted 101-fold (V=50/n). After the culture, the amount of L-threonine that had accumulated in the medium was measured by a known method (liquid chromatography using ODS-2 column, Hitachi).

Composition of L-Threonine Fermentation Medium:

| | |
|---|---|
| glycerol | 40 |
| $(NH_4)_2SO_4$ | 24 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Yeast extract | 2.0 |
| Distilled water | To final volume of 1 L |

The medium was adjusted to pH 6.2 with KOH, and autoclaved at 115° C. for 10 minutes, provided that glycerol and $MgSO_4.7H_2O$ were sterilized separately, and $CaCO_3$ (Japanese Pharmacopoeia) subjected to hot air sterilization at 180° C. for 2 hours was added.

The results are shown in Table 2. In the table, OD, Thr (g/L), and Yield (%) indicate the optical density at 600 nm of the medium, the amount of L-threoinine that had accumulated in a flask, and the yield of threonine from the substrate, respectively. As seen from the table, the L-threonine-producing strain with decreased ribonuclease G activity was able to produce L-threonine in a larger amount as compared to that observed for the unmodified strain.

TABLE 2

| | OD | Thr (g/L) | Yield (%) |
|---|---|---|---|
| B-5318 | 19.21 | 13.8 | 34.5 |
| B-5318Δrng::Tet | 20.66 | 14.0 | 34.8 |

INDUSTRIAL APPLICABILITY

According to the present invention, L-amino acids can be efficiently produced by using inexpensive glycerol as a carbon source.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing an L-amino acid comprising:
   (A) culturing a bacterium in a medium containing glycerol, wherein said bacterium belongs to the family Enterobacteriaceae and is able to produce the L-amino acid, and
   (B) collecting the L-amino acid from the medium, wherein the bacterium has been modified so that the activity of ribonuclease G is decreased, wherein said L-amino acid is L-lysine or L-threonine, and wherein the rng gene coding for said ribonuclease G is inactivated.

2. The method according to claim 1, wherein the rng gene comprises a DNA coding for the amino acid sequence of SEQ ID NO: 2, or a variant thereof.

3. The method according to claim 1, wherein the L-amino acid is L-lysine, and in the bacterium the activity of an enzyme is increased and/or the activity of lysine decarboxylase is decreased; wherein the enzyme is selected from the group consisting of dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, succinyl diaminopimelate deacylase, and combinations thereof.

4. The method according to claim 1, wherein the L-amino acid is L-threonine, and in the bacterium the activity of an enzyme is increased; wherein the enzyme is selected from the group consisting of aspartate semialdehyde dehydrogenase, aspartokinase I, homoserine kinase, aspartate aminotransferase, threonine synthase, and combinations thereof.

5. The method according to claim 1, wherein the bacterium belongs to a genus selected from the group consisting of *Escherichia, Enterobacter*, and *Pantoea*.

6. The method according to claim 1, wherein glycerol is crude glycerol produced in biodiesel fuel production.

7. The method according to claim 1, wherein said bacterium is *Escherichia coli*.

* * * * *